US00PP24730P3

(12) United States Plant Patent
Carmi et al.

(10) Patent No.: US PP24,730 P3
(45) Date of Patent: Aug. 5, 2014

(54) MEDITERRANEAN MANDARIN TREE NAMED 'ODEM'

(50) Latin Name: ***Citrus deliciosa* Ten (ex *C. reticulata* Blanco)**
Varietal Denomination: ODEM

(75) Inventors: Nir Carmi, Ramat Efal (IL); Hanna Neuman-Leshem, Hemed (IL); Ahuva Frydman-Shani, Ramat-Gan (IL); Pinchas Spiegel-Roy, Ramat-Gan (IL); Aliza Vardi, Ramat-Gan (IL); Avraham Elhanati, Holon (IL); Yosef Yaniv, Rehovot (IL); Kanonich Yeoshua, Yavne (IL); Ahuva Daos, Ganey Hmoshava Mazkeret Batia (IL)

(73) Assignee: State of Israel, Ministry of Agriculture & Rural Development, Agricultural Research Organization, Bet Dagan (IL)

( * ) Notice: Subject to any disclaimer, the term of this patent is extended or adjusted under 35 U.S.C. 154(b) by 94 days.

(21) Appl. No.: 13/507,899

(22) Filed: Aug. 6, 2012

(65) Prior Publication Data

US 2014/0041086 P1 Feb. 6, 2014

(51) Int. Cl.
*A01H 5/00* (2006.01)

(52) U.S. Cl.
USPC ..... Plt./202; Plt./156; Plt./201

(58) Field of Classification Search
USPC ..... Plt./156, 201, 202
See application file for complete search history.

(56) References Cited

PUBLICATIONS

Israel Plant Breeders' Rights application No. 3670/04 filed Aug. 5, 2004 for Mediterranean Mandarin named 'ODEM' (5 pgs.).

*Primary Examiner* — Susan McCormick Ewoldt
(74) *Attorney, Agent, or Firm* — Foley & Lardner LLP

(57) ABSTRACT

A new and distinct mandarin variety of *Citrus deliciosa* Ten. named 'ODEM', particularly characterized by easy-peeling, mid-season ripening, high quality flavor, flattened-rounded fruit shape at stalk end, medium size fruit and dark orange-red skin color.

7 Drawing Sheets

Botanical name of the genus and species of the plant claimed: *Citrus deliciosa* Ten (ex *C. reticulata* Blanco).

Variety denomination: 'ODEM'.

BACKGROUND OF THE INVENTION

The present invention relates to a new and distinct variety of a mandarin tree, botanically known as *Citrus deliciosa* Ten., of the Rutaceae Family, and hereinafter referred to by the variety denomination 'ODEM'.

The new *Citrus deliciosa* Ten. variety is a product of a planned breeding program conducted by the inventors, Nir Carmi, Hanna Neuman-Leshem, Ahuva Frydman-Shani, Pinchas Spiegel-Roy, Aliza Vardi, Avraham Elhanati, Yosef Yaniv, Kanonich Yeoshua, and Ahuva Daos, in the Volcani Center, Bet Dagan, Israel. The objective of the breeding program was to develop a new easy peeling, mid-season ripening mandarin variety, with high quality flavor.

The new *Citrus deliciosa* Ten. variety originated from a mutation induced by irradiation, in 1996, of a seedling which resulted from a cross made by the inventors in 1985 in the Volcani Center. The female or seed parent is the *Citrus deliciosa* Ten. designated 'ORAH' (unpatented). The male or pollen parent is the *Citrus deliciosa* Ten. designated 'SHANI' (patented, U.S. Plant Pat. No. 13,634). The new *Citrus deliciosa* Ten. 'ODEM', after irradiation, was observed and further selected, by the inventors, in a controlled environment in 2005 in The Volcani Center.

Asexual propagation of the new *Citrus deliciosa* Ten. variety 'ODEM' by grafting onto 'Troyer' citrange—*Citrus sinensis* (L.) Osb.×*Poncirus trifoliata* L. (unpatented) was first performed in April 1996 in the Volcani Center, and has demonstrated that the combination of characteristics as herein disclosed for the new variety are firmly fixed and retained through successive generations of asexual propagation. The new variety propagates true-to-type.

BRIEF DESCRIPTION OF THE INVENTION

The following traits have been repeatedly observed and are determined to be characteristics of 'ODEM', which in combination, distinguish this mandarin plant as a new, unique and distinct variety:

1. Easy-peeling;
2. Mid-season ripening;
3. High quality flavor;
4. Fruit shape at stalk end flattened-rounded;
5. Medium size fruit; and
6. Dark orange-red skin color.

In comparison to the parental varieties, 'ORAH' (unpatented) and 'SHANI' (patented, U.S. Plant Pat. No. 13,634), 'ODEM' differs primarily in the traits listed in Table 1.

TABLE 1

Comparison of 'ODEM' with parent varieties.

| Trait | New Variety 'ODEM' | Female Parent 'ORAH' (unpatented) | Male Parent 'SHANI' (patented, U.S. Plant Pat. No. 13,634) |
|---|---|---|---|
| Color of rind | dark orange red | orange | orange red |
| Surface | Smooth to medium rough | smooth | smooth |
| Thickness of rind | medium | medium | thin |
| Adherence of rind to flesh | weak | weak | weak |

Of the many commercial varieties known to the present inventors, the most similar in comparison to the new *Citrus deliciosa* Ten. 'ODEM' is *Citrus deliciosa* Ten. 'MURCOTT', in the following characteristics described in Table 2:

TABLE 2

Comparison of 'ODEM' with commercial variety.

| Characteristic | New Variety 'ODEM' | Comparison Variety 'MURCOTT' (unpatented) |
|---|---|---|
| Color of rind | dark orange red | orange |
| Surface | Smooth to medium rough | rough |
| Thickness of rind | medium | thin |
| Adherence of rind to flesh | weak | medium |

BRIEF DESCRIPTION OF THE PHOTOGRAPHS

The accompanying photographs illustrate the overall appearance of the new *Citrus deliciosa* Ten. variety 'ODEM' showing the colors as true as is reasonably possible with colored reproductions of this type. Colors in the photographs may differ slightly from the color values cited in the detailed morphological description, which accurately describe the color of 'ODEM'.

DETAILED MORPHOLOGICAL DESCRIPTION

Figure 1:
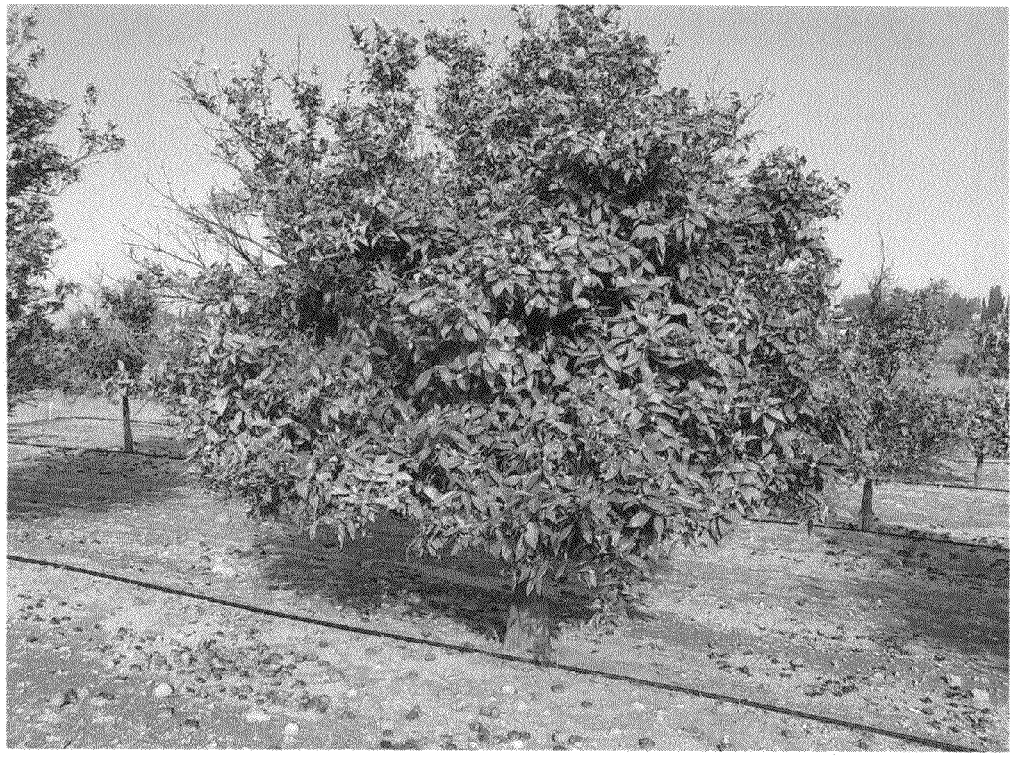
FIG. 1 shows an adult tree of 'ODEM'.
Figure 2:
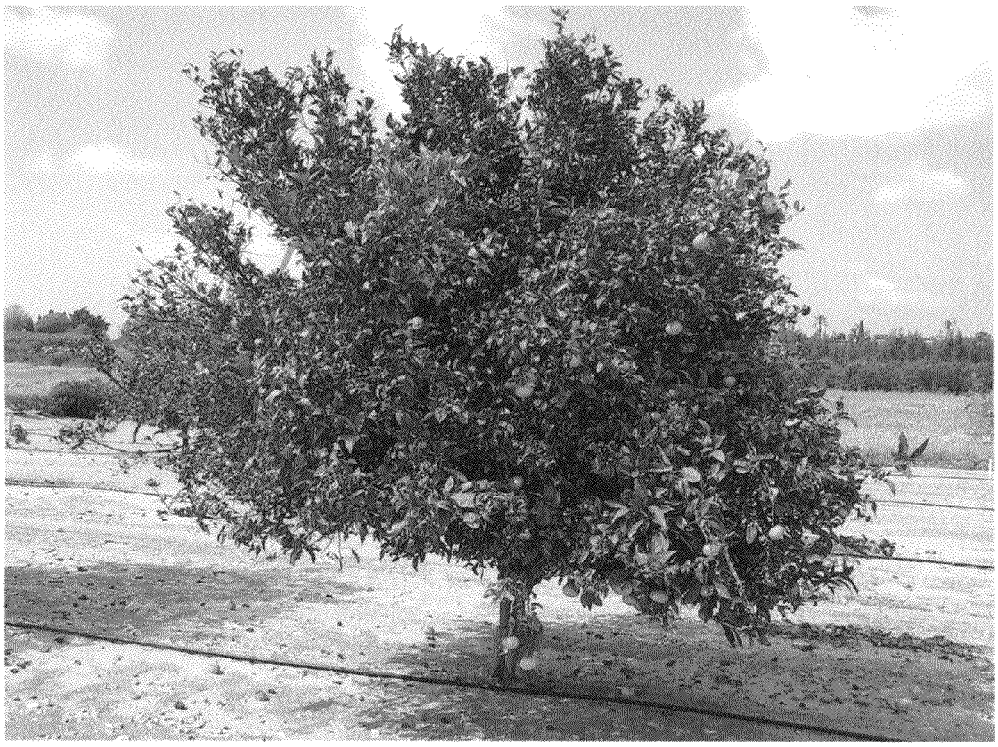
FIG. 2 shows a fruit-bearing tree of 'ODEM'.
Figure 3:
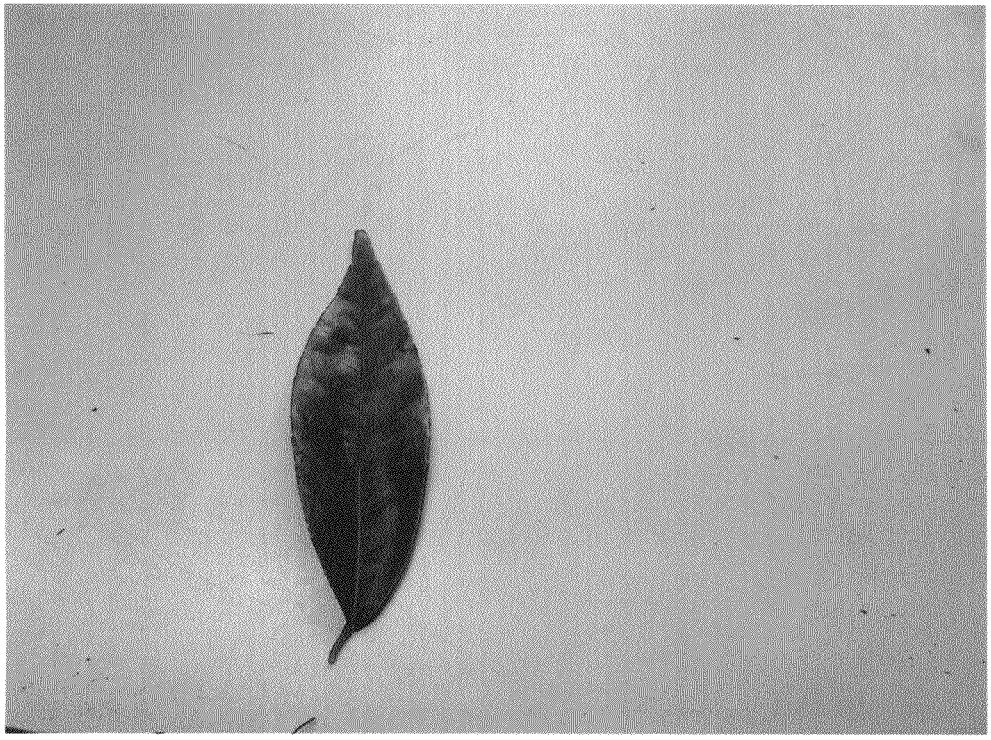
FIG. 3 shows a typical leaf of 'ODEM'
Figure 4:
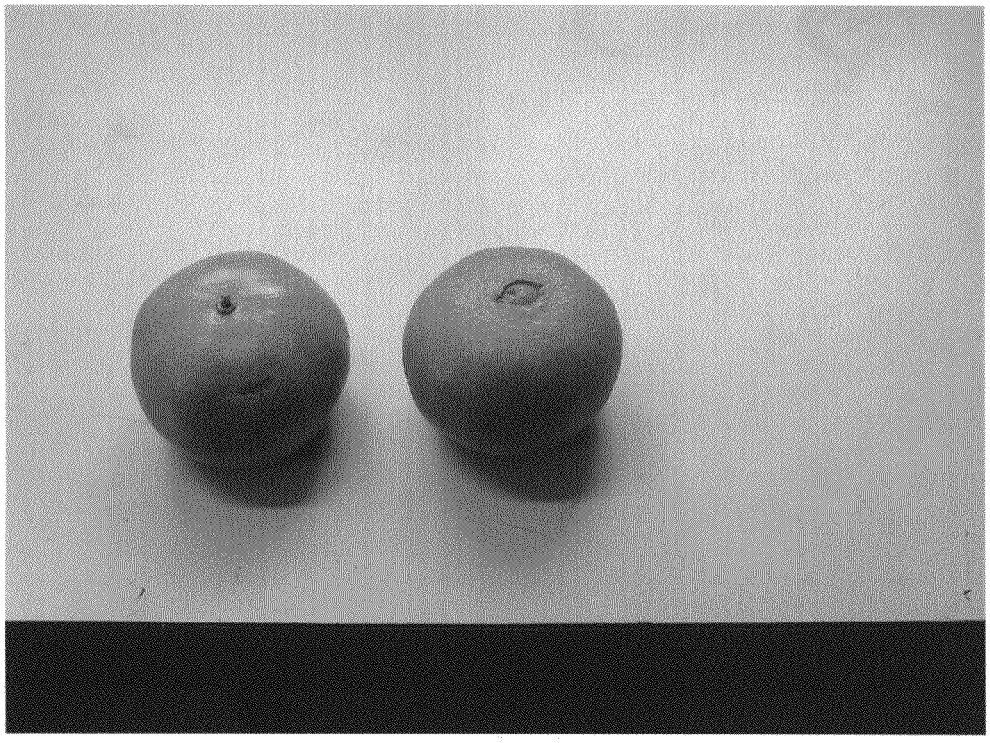
FIG. 4 shows a typical mature fruit of 'ODEM', viewed at base and apex.
Figure 5:
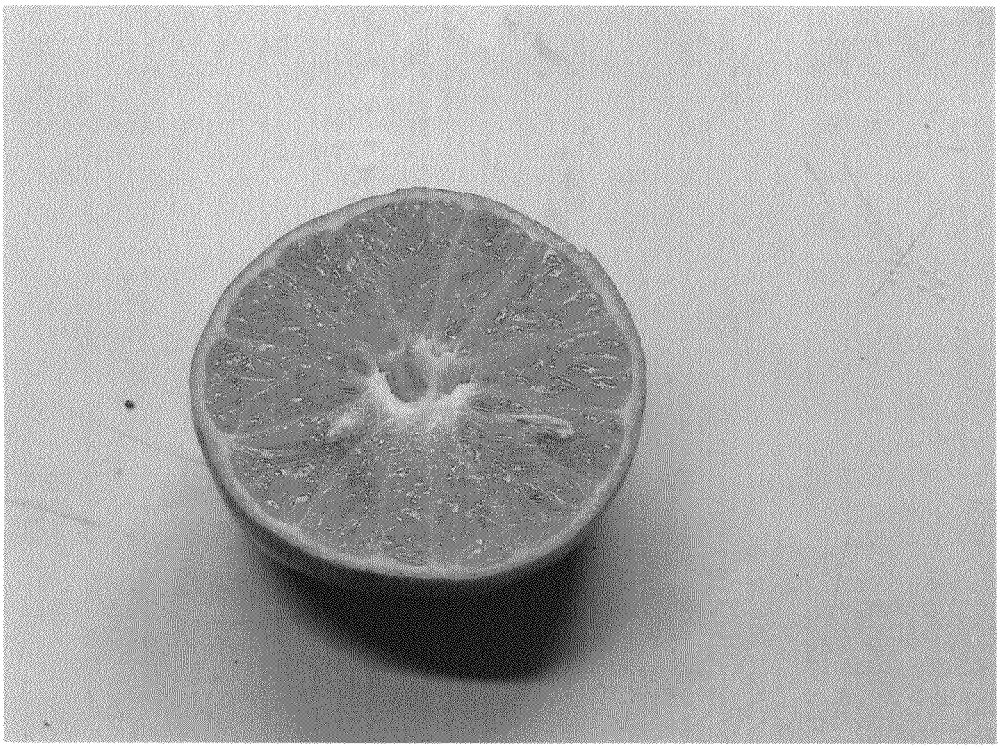
FIG. 5 shows a mature fruit of 'ODEM' in cross section.
Figure 6:
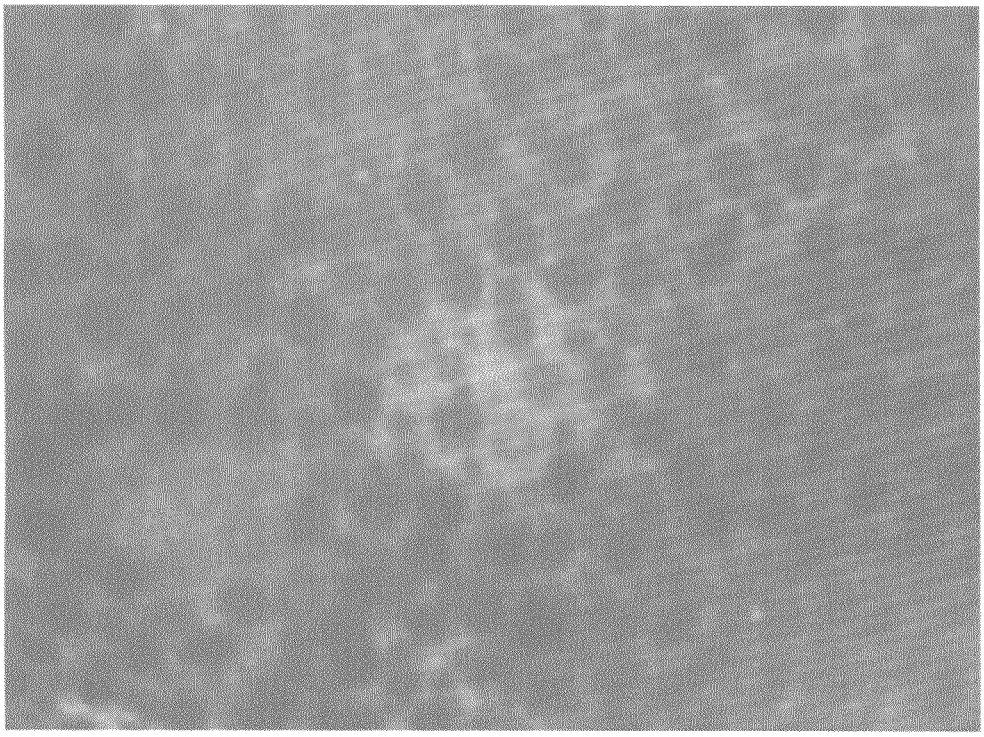
FIG. 6 shows a close-up view of skin oil glands of a mature fruit of 'ODEM'.
Figure 7:
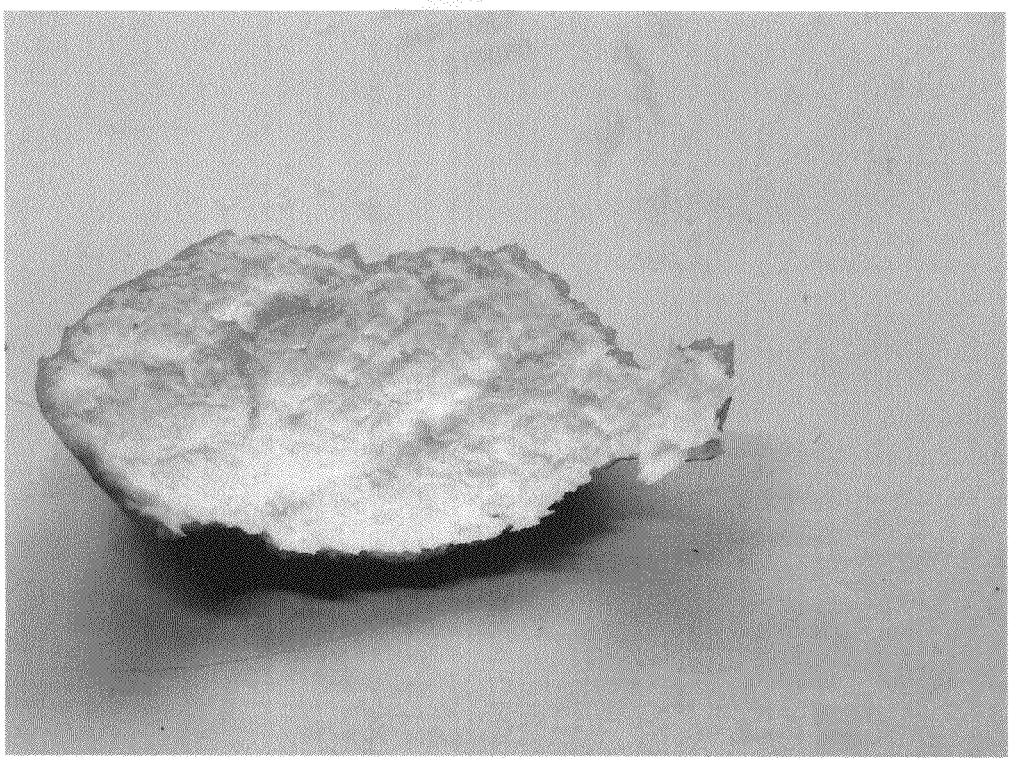
FIG. 7 shows the albedo on the inside peel of a mature fruit of 'ODEM'.

The new *Citrus deliciosa* Ten. 'ODEM' has not been observed under all possible environmental conditions. The phenotype of the new variety may vary with variations in environment such as temperature, light intensity, day length, soil or pruning, without any change in the genotype of the mandarin plant.

The aforementioned photographs, together with the following observations, measurements and values describe plants of 'ODEM' as grown in the orchard in The Volcani Center, under conditions which closely approximate those generally used in commercial practice. "Pardes" the Hebrew word for citrus orchard is derived from the Persian "pairida ēza" which means surrounded by a wall. From the same word the word "paradise" was deducted.

The described trees were grafted on 'Troyer' citrange—*Citrus sinensis* (L.) Osb.×*Poncirus trifoliata* L. (unpatented) and planted at a distance of 1.5×5 m in sandy red loam soil at an elevation of about 30 meters above sea level with Irrigation of 100 $m^3$ per hectare during summer, and addition of 1 liter of fertilizers (7:3:7+micro-elements (trace elements)) per 1 $m^3$ of water. Average annual rainfall is about 550 mm, with an average 350 mm of rainfall in winter (December to February). Mean diurnal minimum temperature in January is 7.2° C., and mean diurnal maximum temperature in July is 30.8° C.

Unless otherwise stated, the detailed morphological description includes observations, measurements and values taken from 2009 to 2011 and based on thirteen-year-old 'ODEM' trees, grafted in 1996 and grown in the orchard in the Volcani Center. Quantified measurements are expressed as an average or a range of measurements taken from a number of plants of 'ODEM'. The measurements of any individual plant, or any group of plants, of the new variety may vary from the stated average or range.

Color references are made to The Royal Horticultural Society Colour Chart (R.H.S.), (1986 edition), except where general colors of ordinary significance are used. Color values were taken under daylight conditions in full sunlight in The Volcani Center, Bet Dagan, Israel.

All of the plants of 'ODEM', insofar as they have been observed, have been consistent in all the characteristics described below.

Classification:

*Botanical.*—*Citrus deliciosa* Ten.

Parentage:

*Female or seed parent.*—*Citrus deliciosa* Ten. 'ORAH' (unpatented).

*Male or pollen parent.*—*Citrus deliciosa* Ten. 'SHANI' (patented U.S. Plant Pat. No. 13,634).

Propagation: Grafting onto 'Troyer' citrange—*Citrus sinensis* (L.) Osb.×*Poncirus trifoliata* L. (unpatented).

Growing conditions:

*Light intensities*.—Full sunlight.

| | January | February | March | April |
|---|---|---|---|---|
| Mean maximum air temperature (° C.) | 17.8 | 18.1 | 20.1 | 24.5 |
| Mean minimum air temperature (° C.) | 7.2 | 7.1 | 8.8 | 11.5 |
| Mean rainfall (mm) | 140.5 | 96.9 | 66.1 | 17.5 |
| | **May** | **June** | **July** | **August** |
| Mean maximum air temperature (° C.) | 27 | 29.2 | 30.8 | 31.2 |
| Mean minimum air temperature (° C.) | 14.6 | 17.9 | 20.6 | 21.2 |
| Mean rainfall (mm) | 2.2 | — | — | — |
| | **September** | **October** | **November** | **December** |
| Mean maximum air temperature (° C.) | 30.4 | 28.3 | 24.1 | 19.7 |
| Mean minimum air temperature (° C.) | 19.4 | 16 | 11.8 | 8.6 |
| Mean rainfall (mm) | 0.4 | 20.4 | 76.2 | 130.3 |

*Fertilization*.—A balanced fertilizer with level of 7:3:7 (N:P:K)+micro-elements.

*Pollination requirements*.—None; variety is parthenocarpic.

*Growth regulators*.—None used.

*Pruning*.—Manual pruning is applied. The size and overall shape of mandarin trees essentially depend on pruning and spacing. 'ODEM' was pruned, creating a tree which is conical to spherical in shape with 4 or 5 main branches. When the trees are freely grown, the size and the shape assumed by the trees are typical of *Citrus deliciosa* Ten.

BOTANICAL CHARACTERISTICS

Age: Observed trees were 13-years-old.

Fruit:
- *Type*.—Mandarin.

Tree:
- *Vigor*.—Strong.
- *Height*.—About 2.5 m.
- *Diameter of crown*.—About 2.5 m.
- *Overall shape*.—Triangular to rounded.
- *Density of canopy*.—Dense.
- *No of main brunches*.—5.
- *Diameter of trunk*.—About 15 cm.
- *Color of bark*.—Very dark gray closest to RHS 201 A.
- *Surface of bark*.—Nearly smooth.
- *Lenticels*.—Not visible.

Main branches:
- *Attitude*.—Semi-upright.
- *Angle relative to trunk*.—About 45°.
- *Length*.—About 2 m.
- *Thickness*.—5-10 cm.
- *Color of bark*.—Very dark gray closest to RHS 201 A.
- *Surface of bark*.—Nearly smooth.
- *Lenticels*.—Not visible.

Young leaf:
- *Anthocyanin coloration*.—Absent.
- *Upper side green color*.—Between RHS 146 A and 146 B.
- *Lower side green color*.—RHS 146 D.
- *Surface*.—Smooth.
- *Glossiness*.—Weak.
- *Pubescence*.—Absent.

Fully developed leaf-blade:
- *Length*.—60-70 mm.
- *Width*.—28-32 cm.
- *Shape in cross section*.—Concave.
- *Twisting*.—Absent.
- *Blistering*.—Medium.
- *Upper side green color*.—RHS 146 A.
- *Lower side green color*.—RHS 146 D.
- *Pubescence on upper side*.—Absent.
- *Pubescence on lower side*.—Absent.
- *Firmness*.—Weak.
- *Undulation of margin*.—Medium.
- *Incisions of margin*.—Crenate.
- *Depth of incisions of margin*.—Shallow.
- *Shape of apex*.—Acute with obtuse to rounded occasional emarginate tip.
- *Shape of base*.—Obtuse.
- *Glossiness*.—Weak.

Petiole:
- *Length*.—12-15 mm.
- *Width of wing*.—1-2 mm.
- *Width of wing relative to leaf blade*.—Very narrow.
- *Shape in cross section*.—Concave.
- *Upper side green color*.—RHS 146 A.
- *Lower side green color*.—RHS 146 D.
- *Pubescence*.—Absent.
- *Surface*.—Smooth.

Petiole wing:
- *Upper side green color*.—RHS 146 A.
- *Lower side green color*.—RHS 146 D.
- *Surface*.—Smooth.

Flower bud:
- *Anthocyanin coloration*.—Absent.
- *Shape*.—Spherical.
- *Color*.—Yellowish white RHS 150 D.
- *Length*.—5-8 mm.
- *Diameter*.—About 5 mm.

Vegetative bud:
- *Anthocyanin coloration*.—Absent.
- *Shape*.—Spherical.
- *Color*.—Very light green RHS 150 A.
- *Length*.—1-2 mm.
- *Diameter*.—1-2 mm.

Flower:
- *No. of petals*.—5.
- *Shape*.—Star-like.
- *Diameter of corolla*.—16-20 mm.
- *Scent*.—Typical for citrus.

Pedicel:
- *Length*.—4-5 mm.
- *Shape in cross section*.—Circular.
- *Color*.—Light green RHS 144 C.
- *Thickness*.—About 1 mm.

Calyx:
- *Diameter*.—About 4 mm.
- *Color*.—Very light green between RHS 145 C and 145 D.
- *Shape*.—Flattened.
- *Shape of apex of lobe*.—Acute.
- *Size*.—Miniscule.

Petal:
- *Shape*.—Elongated.
- *Length*.—10-12 mm.
- *Width*.—5-6 mm.
- *Color of upper side*.—White RHS 155 A.
- *Color of lower side*.—White RHS 155 A.

Stamina:
- *Number*.—About 17.

Anther:
- *Length*.—Less then 1 mm.
- *Color*.—Yellow RHS 13 C.
- *Shape*.—Elongated.

Filament:
- *Length*.—5-7 mm.
- *Thickness*.—Less than 1 mm.
- *Color*.—White RHS 155 A.

Pollen:
- *Color*.—Yellow RHS 13 C.
- *Viability*.—Low.

Style:
- *Length*.—5-6 mm.
- *Diameter*.—1-2 mm.
- *Color*.—Green RHS 144 D.

Stigma:
*Shape*.—Rounded.
*Color*.—Yellow RHS 13 C.
Fruit:
*Length*.—50-58 mm.
*Diameter*.—66-78 mm.
*Ratio length/diameter*.—Shorter than broad.
*Position of maximum diameter*.—In the middle.
*Shape in cross section*.—Rounded scalloped.
*Shape at stalk end*.—Flattened-rounded.
*Depression at stalk end*.—Absent.
*Neck*.—Absent.
*Radial grooves at stalk end*.—Absent.
*Floral disc below calyx*.—Absent.
*Abscission layer between calyx and fruit*.—Absent.
*Shape at distal end*.—Flattened-rounded.
*Depression at distal end*.—Present.
*Depth of depression at distal end*.—Very shallow less than 1 mm.
*Diameter of depression relative to fruit*.—Small.
*Areola*.—Present, complete.
*Conspicuousness of areola*.—Medium.
*Type of areola*.—Smooth.
*Diameter of areola relative to diameter of fruit*.—Large.
*Stylar scar*.—Typical.
*Persistence of style*.—Absent.
*Navel opening*.—Present.
*Diameter of navel opening*.—5-10 mm.
*Protrusion of navel*.—Absent.
*Radial grooves at distal end*.—Absent.
*Main color of surface*.—Dark orange red RHS 32 A.
*Pubescence of surface*.—Absent.
*Glossiness*.—Medium.
*Roughness of surface*.—Smooth to medium rough.
*Evenness of size of oil glands*.—Uneven small and large ones.
*Size of larger oil glands*.—About 1 mm.
*Conspicuousness of larger oil glands*.—Strong.
*Pebbles on oil glands*.—Medium dense.
*Color of oil glands*.—Light orange RHS 23B.
*Firmness*.—Medium.
*Thickness of rind*.—Medium 2-3 mm.
*Adherence of rind to flesh*.—Weak.
*Strength of rind*.—Strong.
*Oiliness of rind*.—Medium.
*Oil glands on inner side*.—Inconspicuous.
*Color of albedo*.—Light orange RHS 27 B.
*Density of albedo*.—Medium.
*Adherence of albedo to flesh*.—Medium.
*Amount of fibers in albedo*.—Few.
*Differently colored spots in flesh*.—None.
*Bicolored segments*.—None.
*Color of flesh*.—Light orange RHS 25 B.
*Filling of core*.—Half filled.
*Diameter of core relative to fruit*.—Medium 10-14 mm.
*Number of non-developed segments*.—Non or very few.
*Number of developed segments*.—Many 11 or 12.
*Number of open segments*.—None.
*Adherence of segments*.—Weak.
*Strength of segment wall*.—Weak.
*Length of juice vesicle*.—4-7 mm.
*Thickness of juice vesicle*.—About 4 mm.
*Conspicuousness of vesicle wall*.—Inconspicuous.
*Adherence of juice vesicles*.—Strong.
*Presence of navel viewed internally*.—Present.
*Length of internal navel*.—Short 6-13 mm.
*Ratio length/diameter of internal navel*.—Small.
*Juice content*.—Medium.
*Total soluble solids*.—15.
*Acidity of juice*.—0.96.
*Strength of fiber*.—Medium.
*Number of seeds*.—None or few, up to 4.
*Poly-embryonic seed*.—Absent.
Seed:
*Length*.—9-13 mm.
*Width*.—6-7 mm.
*Surface* (*when fresh*).—Smooth.
*Prominence of veins or wrinkles*.—Not prominent.
*External color* (*when fresh*).—Greenish white RHS 157 B.
*Color of inner seed coat*.—Greenish white RHS 157 B.
*Color of cotyledons*.—Greenish RHS 145 C.
*External color* (*when dry*).—White RHS 155 B.
*Flowering habit*.—Once per year.
*Fruit ripening*.—January-February.
*Parthenocarpy*.—Present.
*Time of flowering*.—March.
Market use: Mainly for fresh consumption.
Disease resistance: Brown Spot, *Alternaria alternata* pv. *citri* pathotype tangarin Solel.
Pest resistance: No atypical resistance has been noted.
Disease susceptibility: None observed.
Pest susceptibility: None observed.

We claim:

1. A new and distinct mandarin variety of *Citrus deliciosa* Ten. named 'ODEM', as illustrated and described herein.

* * * * *